United States Patent
McBroom et al.

(10) Patent No.: US 8,324,585 B2
(45) Date of Patent: Dec. 4, 2012

(54) DIGITAL IMAGE DETECTOR

(75) Inventors: Gary V. McBroom, Dousman, WI (US); Nicholas Ryan Konkle, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 594 days.

(21) Appl. No.: 12/463,956

(22) Filed: May 11, 2009

(65) Prior Publication Data

US 2010/0284521 A1    Nov. 11, 2010

(51) Int. Cl.
*H01L 27/146* (2006.01)

(52) U.S. Cl. .................................. 250/370.09

(58) Field of Classification Search ........ 250/370.01–370.15; 378/98.8
See application file for complete search history.

(56) References Cited

U.S. PATENT DOCUMENTS

| | | | |
|---|---|---|---|
| 5,804,832 A * | 9/1998 | Crowell et al. ............... | 250/580 |
| 5,906,506 A * | 5/1999 | Chang et al. .................. | 439/500 |
| 6,107,811 A * | 8/2000 | Caudill et al. ................. | 324/713 |
| 6,744,062 B2 * | 6/2004 | Brahm et al. .................. | 250/584 |
| 6,855,936 B2 * | 2/2005 | Yamamoto .............. | 250/370.09 |
| 7,488,943 B2 | 2/2009 | Rose et al. | |
| 7,593,507 B2 | 9/2009 | Ohta et al. | |
| 2004/0114725 A1 | 6/2004 | Yamamoto | |
| 2006/0151211 A1 * | 7/2006 | Coenen et al. ................. | 175/19 |
| 2008/0240358 A1 | 10/2008 | Utschig | |
| 2008/0299843 A1 * | 12/2008 | Hine et al. ........................ | 440/9 |
| 2009/0116431 A1 | 5/2009 | Cadieux | |

FOREIGN PATENT DOCUMENTS

JP        11144792        * 5/1999

OTHER PUBLICATIONS

U.S. Appl. No. 12/403,551, filed Mar. 13, 2009, inventor Liu et al.
U.S. Appl. No. 12/414,848, filed Mar. 31, 2009, inventor Liu et al.
Thales Components & Subsystems, "Pixium Portable 3543," Mar. 2008, Velizy Cedex, France.
Office Action mailed May 5, 2010 for U.S. Appl. No. 12/403,551, filed Mar. 13, 2009 (Applicants: James Zhengshe Liu et al.).
Office Action mailed Jan. 22, 2010 for U.S. Appl. No. 12/414,848, filed Mar. 31, 2009 (Applicants: James Zhengshe Liu et al.).

* cited by examiner

*Primary Examiner* — Kiho Kim
(74) *Attorney, Agent, or Firm* — Fletcher Yoder, P.C.

(57) ABSTRACT

A digital detector of a digital imaging system is provided. In one embodiment, a digital detector includes a detector array disposed in a housing and configured to generate image data based on received radiation. The digital detector may also include a battery configured to be disposed within a receptacle of the housing and to supply operating power to the detector array. In one embodiment, the battery or the detector may provide for wireless data communication. In certain embodiments, a tethered plug configured to be disposed within the receptacle may be provided. In one such embodiment, the tether may be rotatable relative to the plug. Additional systems, methods, and devices are also disclosed.

16 Claims, 9 Drawing Sheets

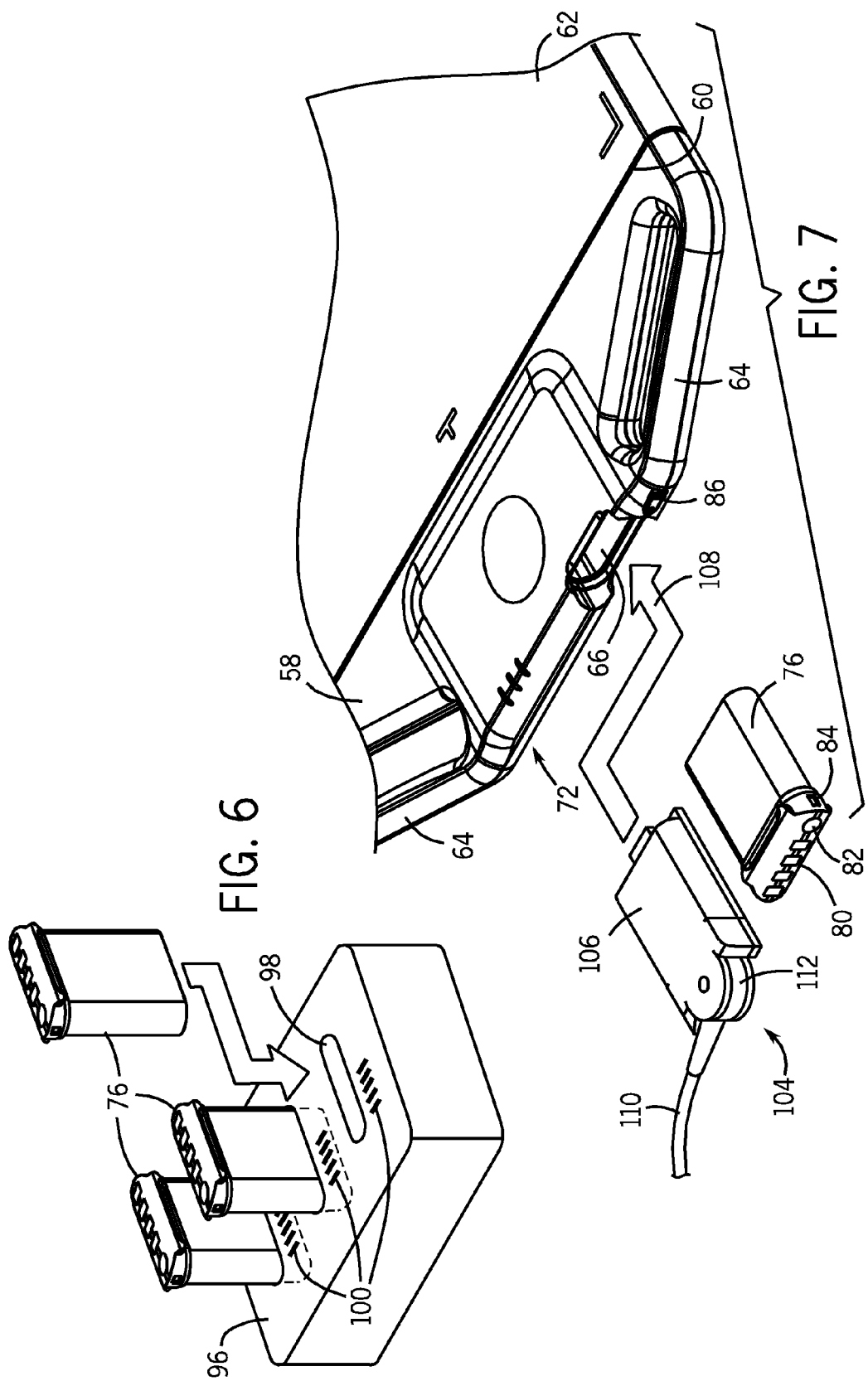

DIGITAL IMAGE DETECTOR

BACKGROUND

The present disclosure generally relates to digital imaging systems, and particularly to a portable digital detector of such systems.

A number of radiological imaging systems of various designs are known and are presently in use. Such systems generally are based upon generation of X-rays that are directed toward a subject of interest. The X-rays traverse the subject and impact a film or a digital detector. In medical diagnostic contexts, for example, such systems may be used to visualize internal tissues and diagnose patient ailments. In other contexts, parts, baggage, parcels, and other subjects may be imaged to assess their contents and for other purposes.

Increasingly, such X-ray systems use digital circuitry, such as solid-state detectors, for detecting the X-rays, which are attenuated, scattered or absorbed by the intervening structures of the subject. Solid-state detectors may generate electrical signals indicative of the intensities of received X-rays. These signals, in turn, may be acquired and processed to reconstruct images of the subject of interest.

To provide greater versatility, some digital detectors are configured as portable devices, in contrast to others that are fixed at a particular location, such as a table or wall stand. In some applications, portable digital detectors may receive power and communicate data via a cable or tether that connects the portable digital detector to other components of an imaging system, such as a computer or image processor. While such a tethered arrangement may provide somewhat increased flexibility in the positioning of the detector, the tether may in some cases interfere with the desired positioning and operation of the detector. In other instances, digital detectors that have an internal battery and communicate wirelessly may also be used. While such wireless detectors may not require a tether for operating power or communication, these wireless detectors may communicate data at a slower rate than some tethered detectors, and may require periodic recharging of their internal batteries, leading to downtime in which the detectors may not be used. Such recharging of internal detector batteries may also result in undesirable heat generation within the detector, and may impair the longevity of the battery due to frequent recharging.

BRIEF DESCRIPTION

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

Some embodiments of the present invention may generally relate to a digital detector for an imaging system. In one embodiment, a digital detector configured for use with an imaging system includes a user-accessible connector configured to alternatively receive a removable battery or a tethered plug, each of which may provide operating power to the detector. When a battery is installed in the connector, the digital detector may acquire image data and may wirelessly communicate such data to one or more other components of the imaging system. In some embodiments, the battery may be externally accessible to a user, allowing the battery to be removed from the connector and replaced with either the tethered plug or an additional battery. In some embodiments, the tethered plug includes a rotatable structure that allows an attached cable to swivel in at least one dimension with respect to the plug. In certain embodiments, the digital detector may also be provided with two offset handles, allowing manipulation and carrying using one or two hands.

Various refinements of the features noted above may exist in relation to various aspects of the present invention. Further features may also be incorporated in these various aspects as well. These refinements and additional features may exist individually or in any combination. For instance, various features discussed below in relation to one or more of the illustrated embodiments may be incorporated into any of the above-described aspects of the present invention alone or in any combination. Again, the brief summary presented above is intended only to familiarize the reader with certain aspects and contexts of the present invention without limitation to the claimed subject matter.

DRAWINGS

These and other features, aspects, and advantages of the present invention will become better understood when the following detailed description is read with reference to the accompanying drawings in which like characters represent like parts throughout the drawings, wherein.

Figure 3:
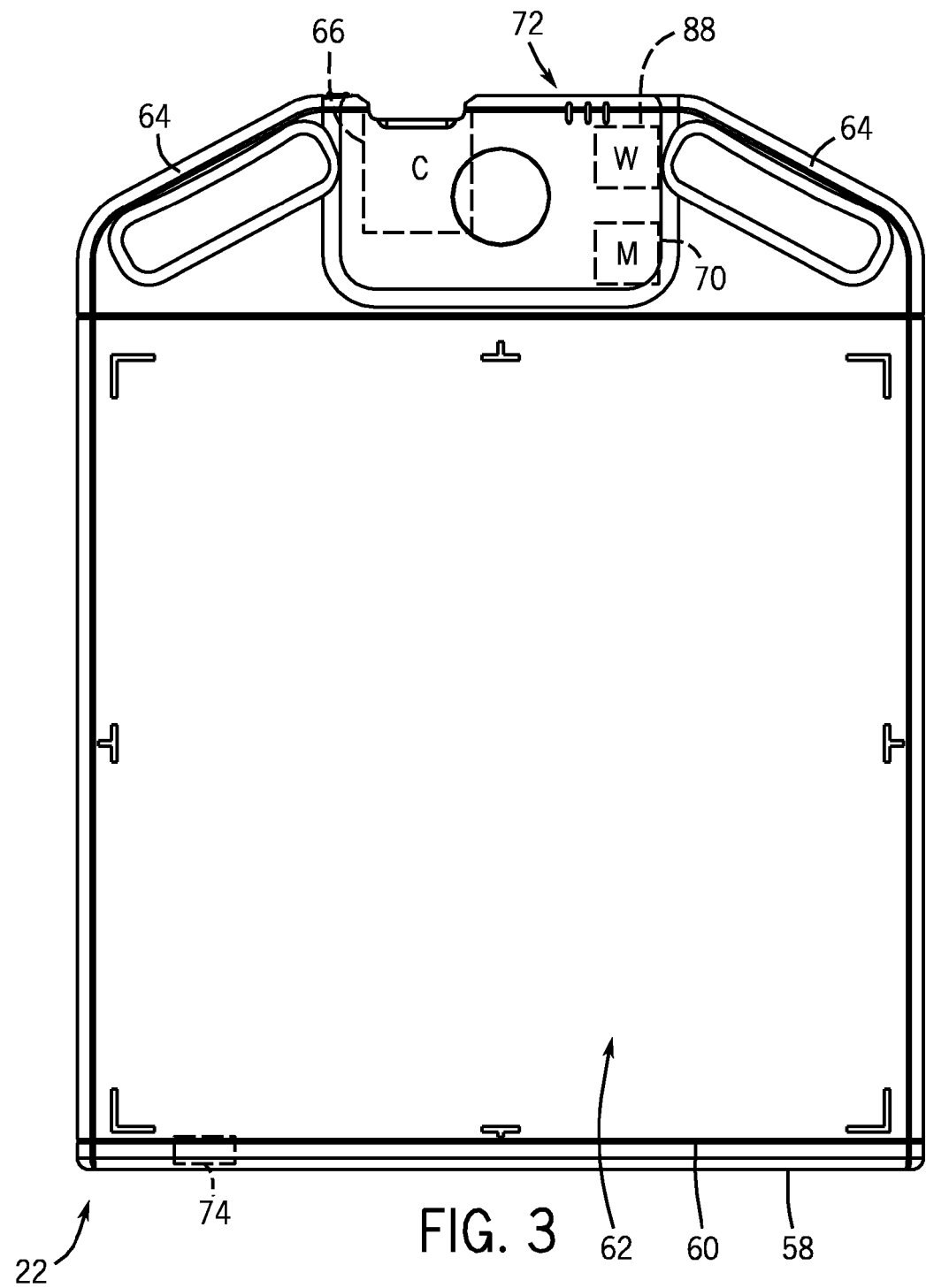
FIG. 3 is an elevational view generally depicting certain features of one embodiment of a digital detector that may be used to acquire image data regarding a patient or object of interest.
Figure 4:
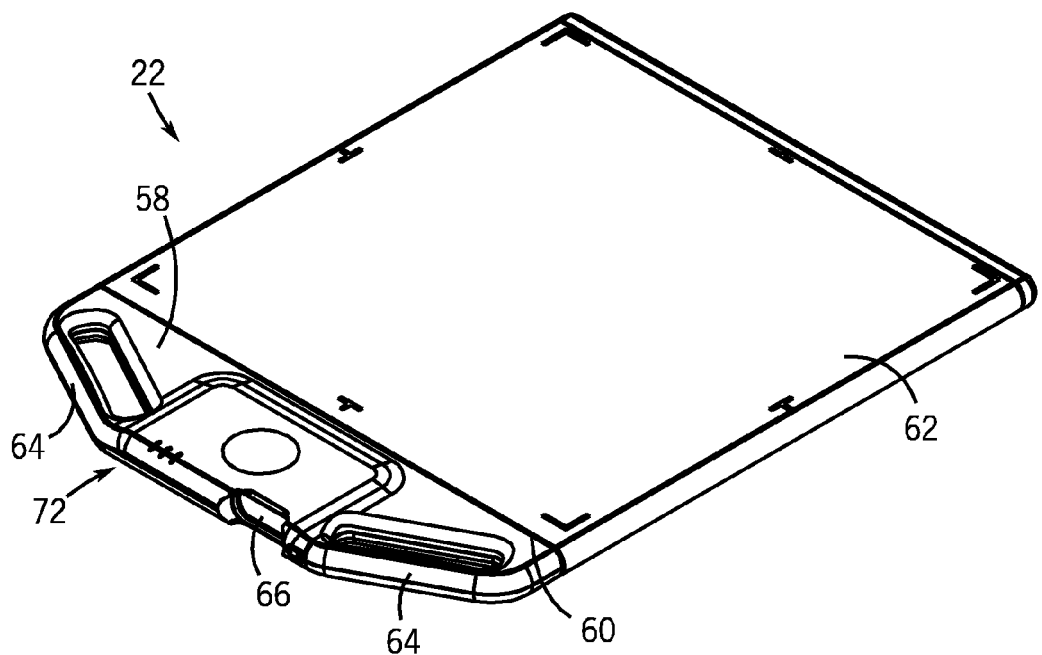
FIG. 4 is a perspective view of the digital detector of FIG. 3, generally depicting a receptacle for receiving either of a removable battery or a tether in accordance with one embodiment.
Figure 5:
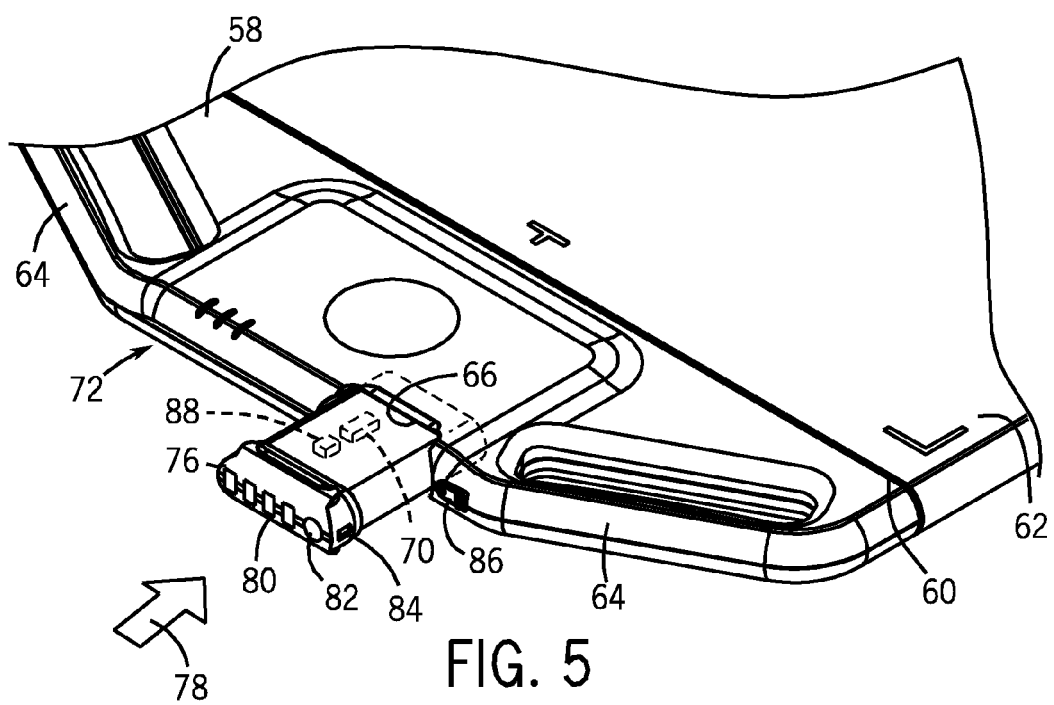
Figure 8:
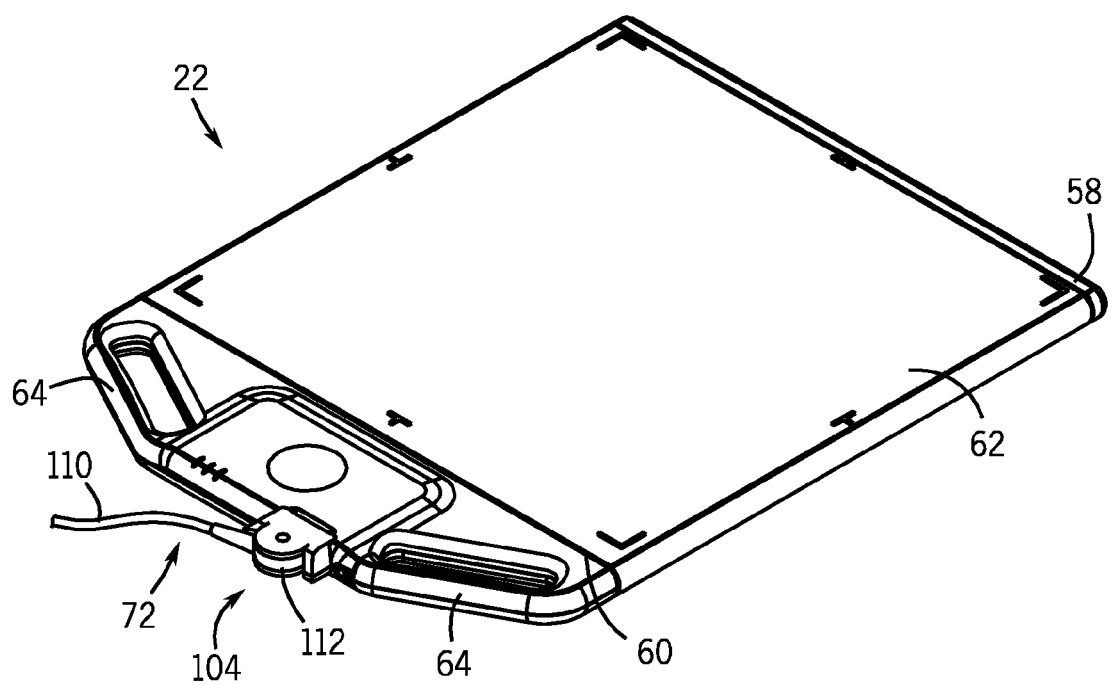
Figure 9:
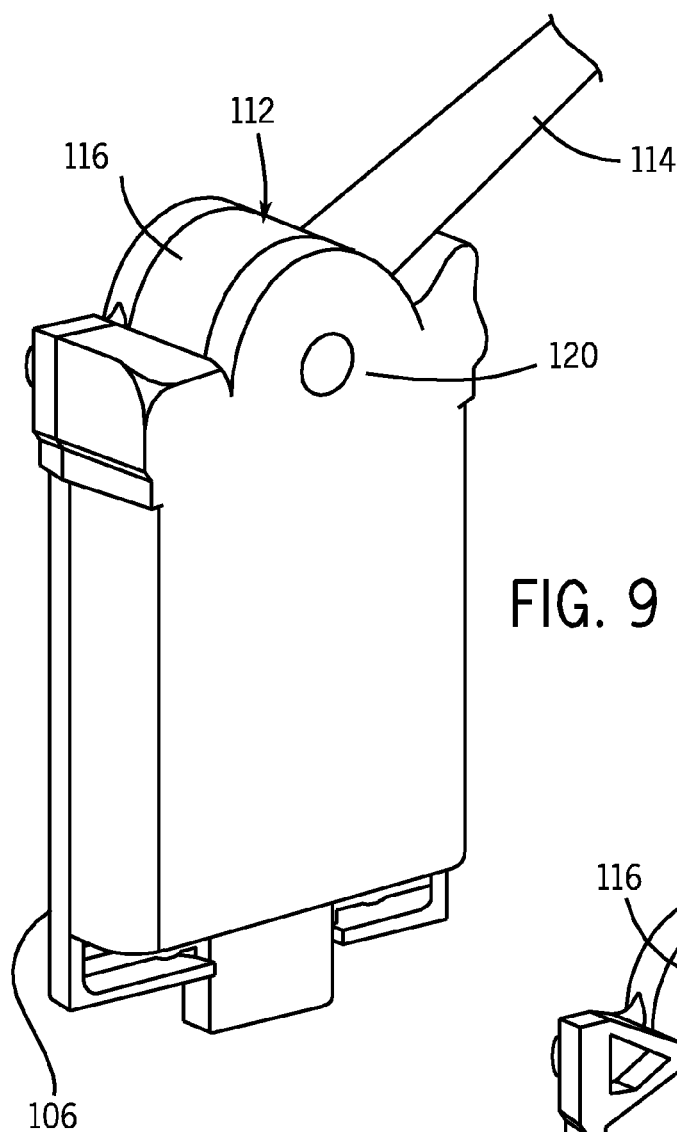
Figure 10:
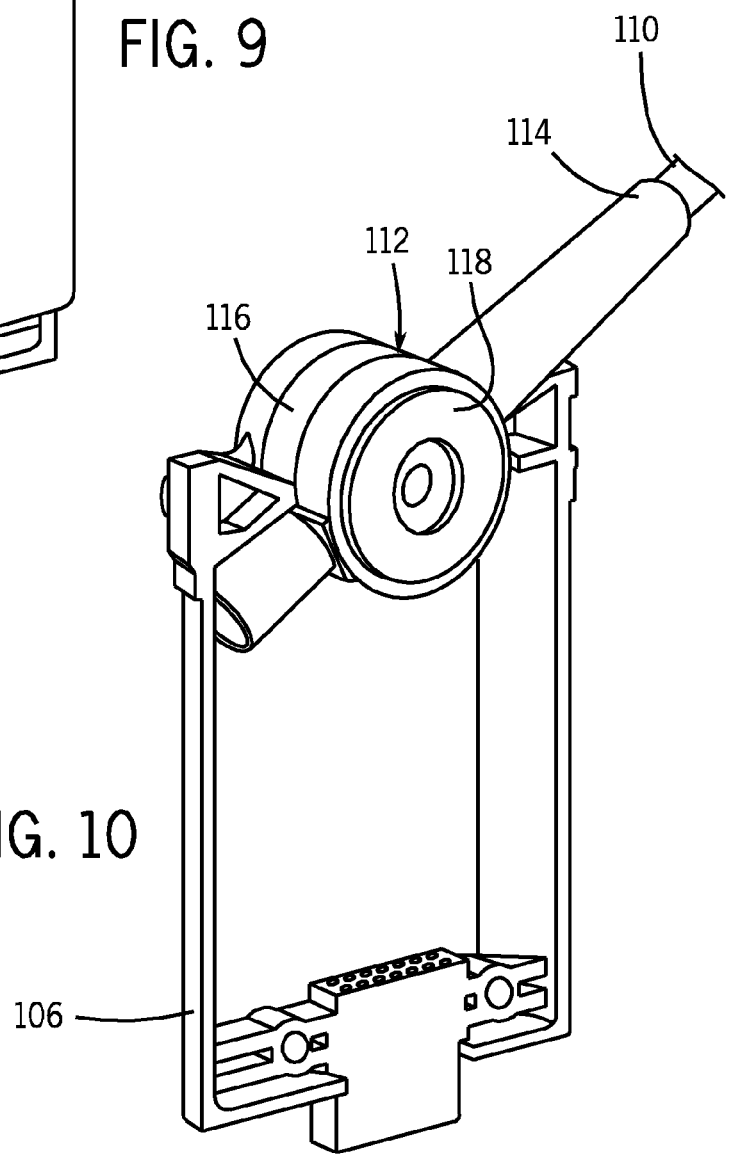
Figure 11:
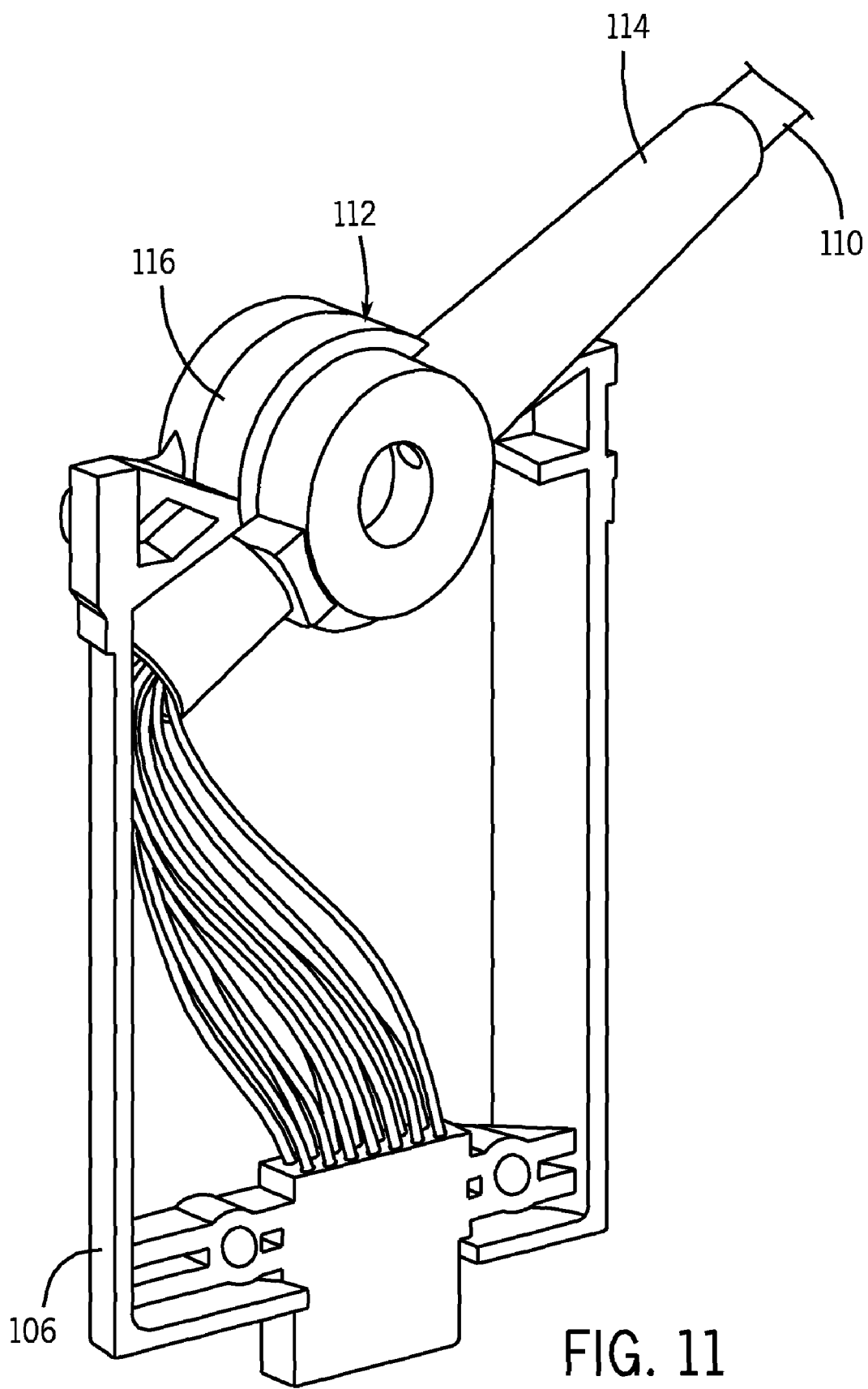
Figure 12:
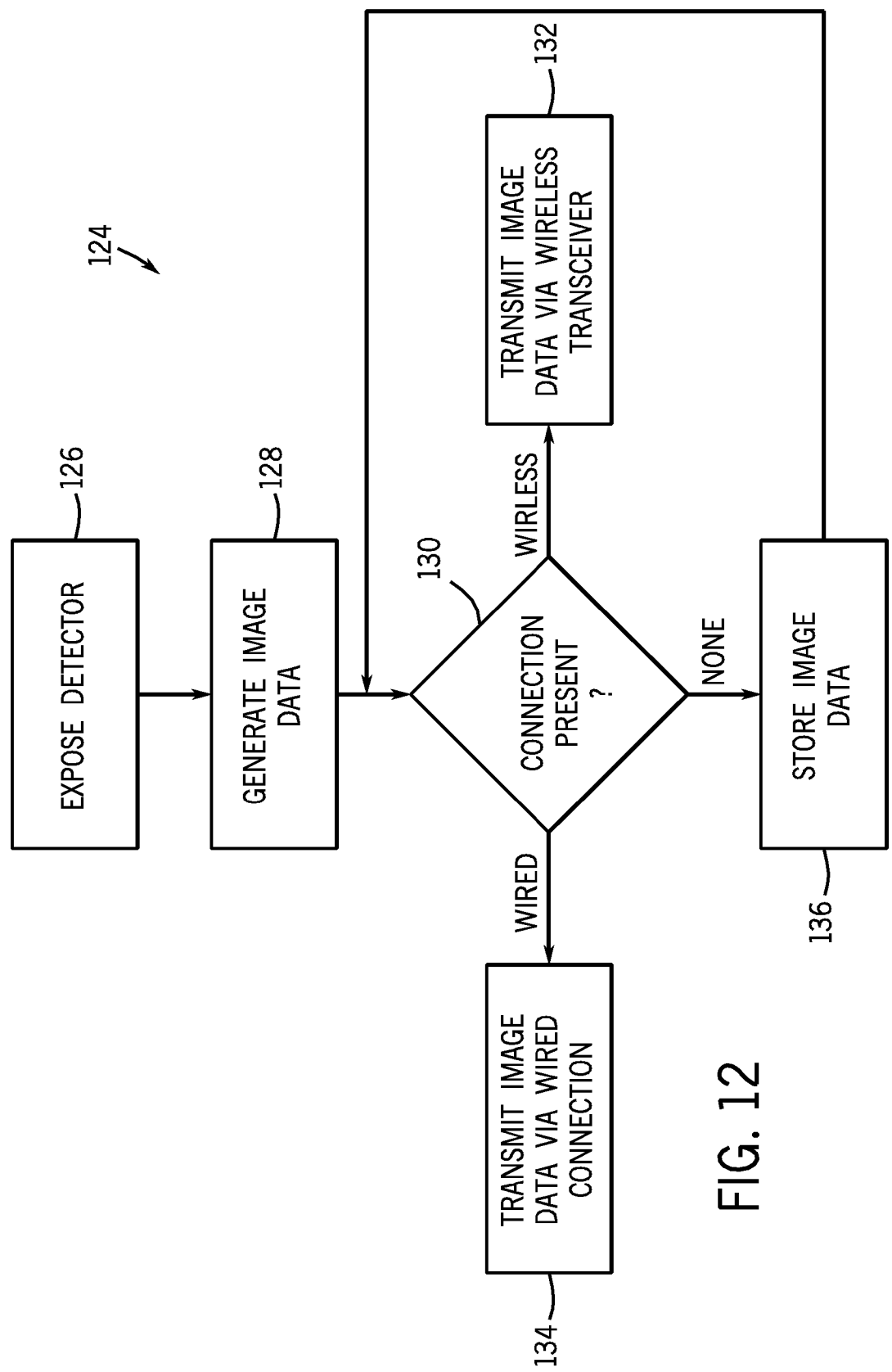

FIG. 5 generally depicts one example of a removable battery, and the insertion of the removable battery into the receptacle generally illustrated in FIG. 4;

FIG. 6 is a perspective view of a charging station for one or more removable batteries for the digital detector of FIG. 3 in accordance with one embodiment;

FIG. 7 generally depicts the removal of the battery of FIG. 5 from the receptacle of the digital detector, and the insertion of a tether into the receptacle in accordance with one embodiment;

FIG. 8 is a perspective view of the digital detector of FIG. 3 having the tether coupled thereto in accordance with one embodiment;

FIG. 9 is a view of a plug having a rotating tether, in accordance with one embodiment;

FIG. 10 is a view of the plug of FIG. 9 showing certain internal structures, in accordance with one embodiment;

FIG. 11, is a view of the plug of FIG. 10 showing a partial cut-away view of a rotating structure of the rotating tether, in accordance with one embodiment; and FIG. 12 is a flowchart of a method of operating an imaging system to acquire image data via a digital detector and to communicate such data from the detector in accordance with one embodiment.

DETAILED DESCRIPTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed technique, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

Figure 1:
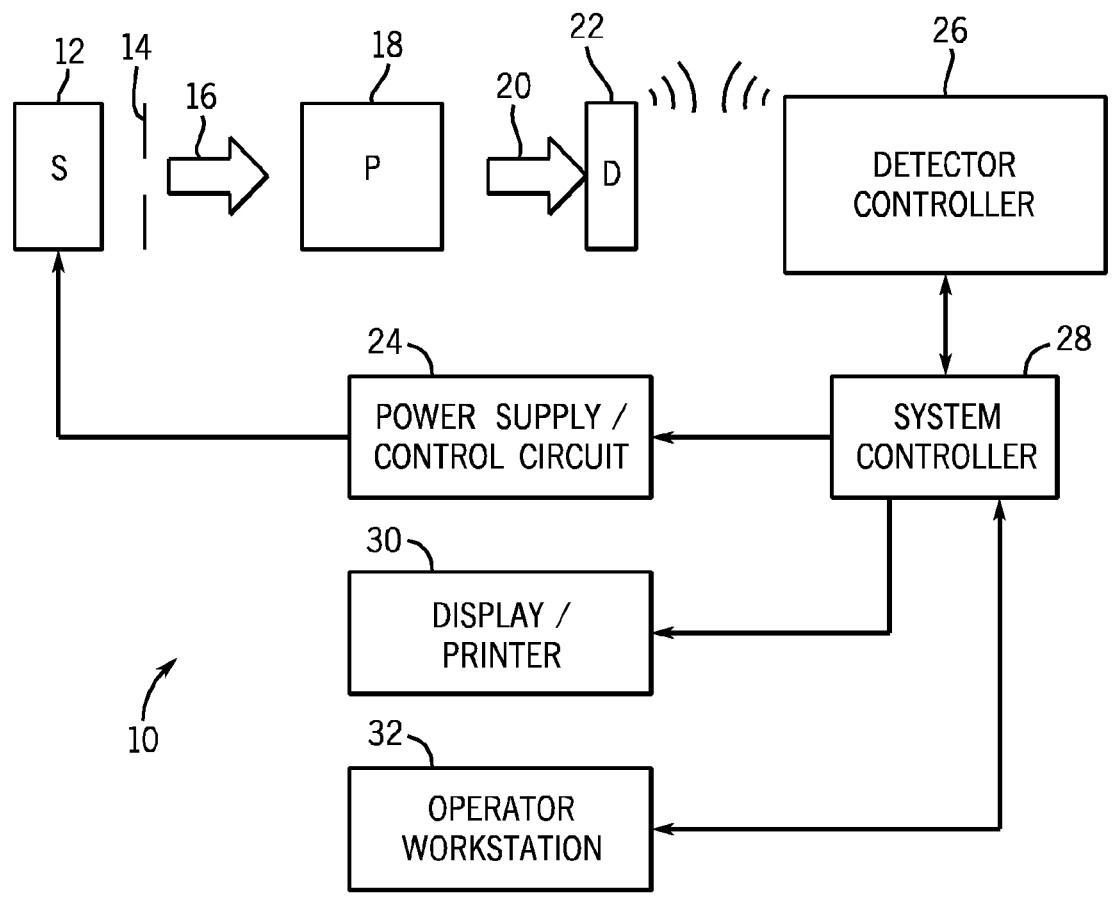
FIG. 1 is a diagrammatical overview of a digital X-ray imaging system of one embodiment in which the present technique may be utilized.

Turning now to the drawings, FIG. 1 illustrates diagrammatically an imaging system 10 for acquiring and processing discrete pixel image data. In the illustrated embodiment, the imaging system 10 is a digital X-ray system designed both to acquire original image data and to process the image data for display in accordance with the present technique. In the embodiment illustrated in FIG. 1, imaging system 10 includes a source of X-ray radiation 12 positioned adjacent to a collimator 14. The collimator 14 permits a stream of radiation 16 to pass into a region in which an object or subject, such as a patient 18, is positioned. A portion of the radiation 20 passes through or around the subject and impacts a digital X-ray detector, represented generally at reference numeral 22. As will be appreciated by those skilled in the art, the detector 22 may convert the X-ray photons incident on its surface to lower energy photons, and subsequently to electric signals, which are acquired and processed to reconstruct an image of the features within the subject.

The radiation source 12 is controlled by a power supply/control circuit 24 which supplies both power and control signals for examination sequences. Moreover, the detector 22 is communicatively coupled to a detector controller 26 which commands acquisition of the signals generated in the detector 22. In one embodiment, the detector 22 may communicate with the detector controller 26 via a suitable wireless communication standard, although the use of detectors 22 that communicate with the detector controller 26 through a cable or some other wired connection are also envisaged. The detector controller 26 may execute various signal processing and filtration functions, such as for initial adjustment of dynamic ranges, interleaving of digital image data, and so forth.

Both the power supply/control circuit 24 and the detector controller 26 are responsive to signals from a system controller 28. In general, the system controller 28 commands operation of the imaging system 10 to execute examination protocols and to process acquired image data. In the present context, the system controller 28 also includes signal processing circuitry, typically based upon a programmed general purpose or application-specific digital computer; and associated manufactures, such as optical memory devices, magnetic memory devices, or solid-state memory devices, for storing programs and routines executed by a processor of the computer to carry out various functionalities, as well as for storing configuration parameters and image data; interface circuits; and so forth. In one embodiment, a general or special purpose computer system may be provided with hardware, circuitry, firmware, and/or software for performing the functions attributed to one or more of the power supply/control circuit 24, the detector controller 26, and/or the system controller 28 as discussed herein.

In the embodiment illustrated in FIG. 1, the system controller 28 is linked to at least one output device, such as a display or printer as indicated at reference numeral 30. The output device may include standard or special purpose computer monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
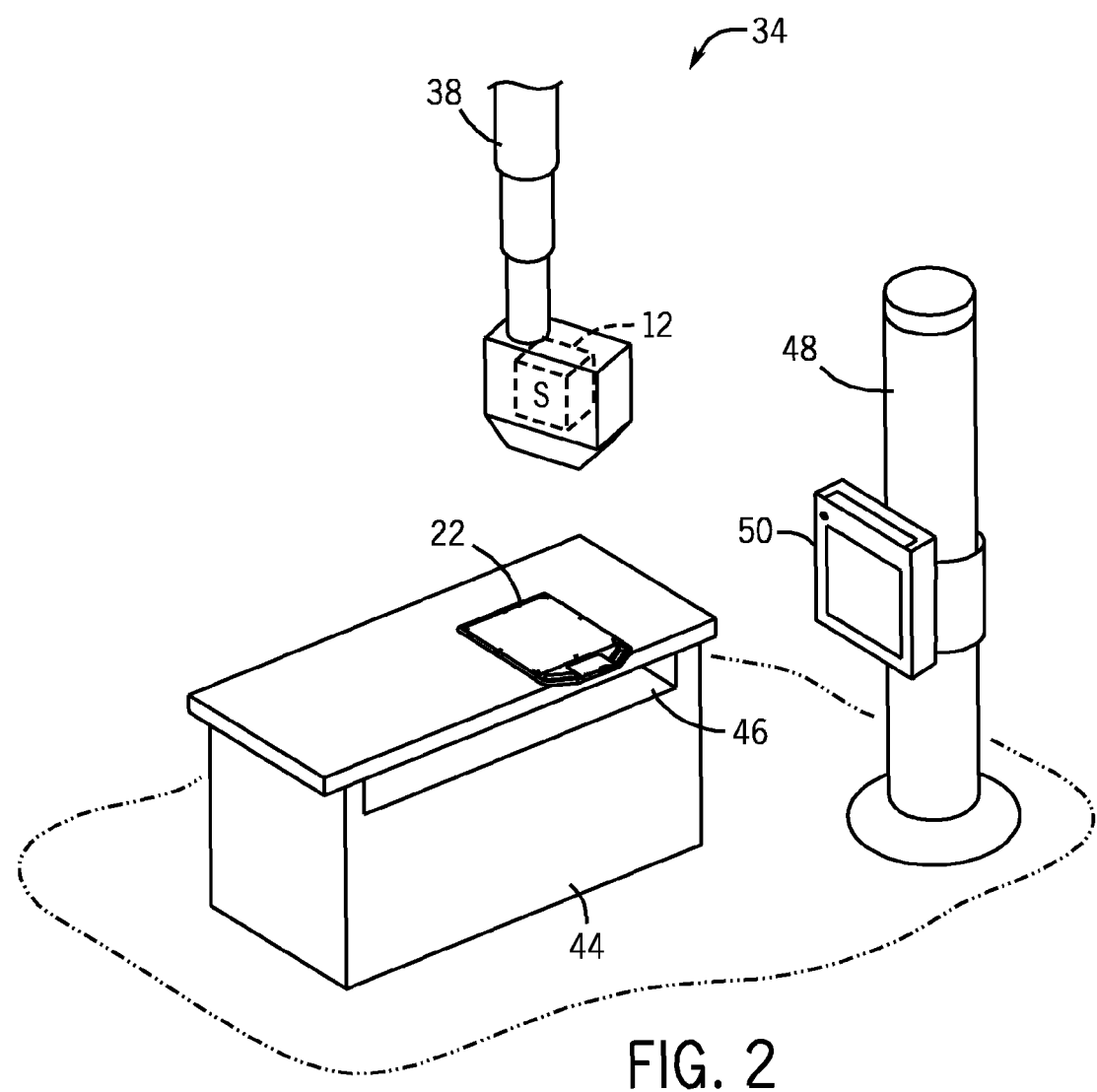
FIG. 2 is a perspective view of the digital X-ray imaging system of FIG. 1 in accordance with one embodiment.

By way of further example, a perspective view of an imaging system 34 is provided in FIG. 2 in accordance with one embodiment. The imaging system 34 includes an overhead tube support arm 38 for positioning a radiation source 12, such as an X-ray tube, with respect to a patient 18 and a detector 22. It is also noted that, in addition to the radiation source 12, the imaging system 34 may also include any or all of the other components described above with respect to FIG. 1, such as the system controller 28.

Moreover, in one embodiment, the imaging system 34 may be used with one or both of a patient table 44 and a wall stand 48 to facilitate image acquisition. Particularly, the table 44 and the wall stand 48 may be configured to receive one or more digital detectors 22. For instance, a digital detector 22 may be placed on the upper surface of the table 44, and the patient 18 (more specifically, an anatomy of interest of the patient 18) may be positioned on the table 44 between the detector 22 and the radiation source 12. In some other instances, the detector 22 may be positioned in a slot 46 below the upper surface of the table 44 and the patient 18, or the radiation source 12 and the detector 22 may be positioned horizontally about the patient 18 for cross-table imaging. Further, the wall stand 48 may include a receiving structure 50 also adapted to receive the digital detector 22, and the patient 18 may be positioned adjacent the wall stand 48 to enable image data to be acquired via the digital detector 22.

In one embodiment, the imaging system 34 may be a stationary system disposed in a fixed X-ray imaging room, such as that generally depicted in, and described above with respect to FIG. 2. It will be appreciated, however, that the presently disclosed techniques may also be employed with other imaging systems, including mobile X-ray units and systems, in other embodiments. For instance, in other embodiments, a mobile X-ray unit may be moved to a patient recovery room, an emergency room, a surgical room, or the like to enable imaging of a patient without requiring transport of the patient to a dedicated (i.e., fixed) X-ray imaging room.

One example of a digital detector 22 is generally illustrated in FIGS. 3 and 4 in accordance with one embodiment. In this presently illustrated embodiment, the detector 22 may include a housing 58 that encloses various components of the detector 22. The housing 58 may include a window 60 that exposes a solid-state detector array 62 within the housing 58. The detector array 62 may be configured to receive electromagnetic radiation, such as from the radiation source 12, and to convert the radiation into electrical signals that may be interpreted by the imaging system 34 to output an image of an object or patient 18. The housing 58 may also include one or more handles 64 that facilitate positioning and transport of the detector 22 by a technician or other user.

For example, in one embodiment, the housing 58 may include two handles 64 set apart from one another. In one such embodiment, the handles 64 may be provided at an angle relative to the main body of the detector 22 to provide improved ergonomics. For example, the two handles 64 may be provided at an ergonomic angle such that when a user holds the detector 22 the center of gravity of the detector 22 is below either handle 64. In this example, a user may hand the detector 22 to another user with relative ease, i.e., by holding one handle 64 while the other user grasps the other handle 64 and/or two users may jointly position the detector 22, each using a different handle 64.

In one embodiment, operating power may be provided to the digital detector 22 via a connector 66 configured to engage either a removable battery or a cable (e.g., a tether), as discussed in greater detail below. In one embodiment, the connector 66 may generally include a receptacle for receiving either the removable battery or the tether and may include electrical contacts to route power from the battery or from an external power source via the tether to the various components of the digital detector 22. The digital detector 22 may communicate with one or more other components of the imaging system 34, such as the system controller 28, via a wireless transceiver 88. In one embodiment, the wireless transceiver 88 may be incorporated into the body of the detector 22 or may, in another embodiment, be incorporated into a removable battery. It is noted that the wireless transceiver 88 may utilize any suitable wireless communication protocol, such as an ultra wideband (UWB) communication standard, a Bluetooth communication standard, or any 802.11 communication standard. Additionally, the digital detector 22 may also communicate data over a wired connection, such as via a tether coupled to the digital detector 22 by way of the connector 66, or via another cable coupled to a docking connector 74 provided elsewhere on the digital detector 22. In this manner, the digital detector 22 may be powered by a battery but still transmit data at a high throughput via a wired connection through the docking connector 74.

Still further, in one embodiment, the digital detector 22 may include a memory device 70. In other embodiments, the memory device 70 may be provided as part of a removable battery, as discussed below. Among other things, the memory device 70 may store image data acquired via the detector array 62. In various embodiments, the memory device 70 may include an optical memory device, a magnetic memory device, or a solid state-memory device. Additionally, in at least one embodiment, the memory device 70 may be a non-volatile memory device, such as a flash memory. The memory device 70 may be internally or externally located with respect to the housing 58 and, depending on the embodiment, may or may not be configured to facilitate user-removal of the memory device 70 from the housing 58. Further, while the connector 66, the wireless transceiver, and/or the memory device 70 may generally be located in one end of the detector 22 as illustrated in FIG. 3, the present technique is not limited to such positions. Rather, these components may be provided at any suitable location of the detector 22 in full accordance with the present techniques. Indeed, as noted above, in certain embodiments, one or both of the wireless transceiver and/or the memory device 70 may be provided as part of a removable battery 76 that may be inserted into or otherwise couple with the detector 22. Additionally, in some embodiments, the housing 58 may include various indicators 72, such as light-emitting diodes, that communicate detector power, status, operation, or the like to a user.

As noted above, in one embodiment, a removable battery 76 may be inserted (as generally indicated by reference numeral 78) into a receptacle of the connector 66, as generally illustrated in FIG. 5. In one embodiment, the removable battery 76 may be a 11.1 V, 1.65 Ah Li-Ion battery. In other embodiments, the removable battery 76 may have higher or lower capacity. The battery 76 may include a power indicator 80 that provides a user with an indication of the amount of remaining battery power. In the presently illustrated embodiment, the power indicator 80 includes a visual power indicator, such as one or more LED lights, an LCD display, or the like, that generally communicates information regarding the remaining charge of the removable battery 76, although the power indicator 80 of other embodiments may also or instead include an auditory power indicator. A visual power indicator 80 may include a series of LED lights that generally represent the remaining charge on the battery 76, or may include a LCD or some other display that outputs the percentage of remaining power left.

In the presently illustrated embodiment, the connector 66 is provided at an edge of the detector 22 such that the battery 76 is received in a manner generally parallel to the plane of the detector (i.e., generally perpendicular to the normal of the detecting surface of the detector 22). In such an embodiment, providing the power indicator 80 on a distal end of the battery 76 that remains externally viewable once installed in the connector 66 may allow a user to more easily determine the remaining charge of the battery 76, even during use of the detector 22. Although the power indicator 80 is presently depicted as located on one end of the battery 76, it is noted that the power indicator 80 may also or instead be positioned on the other sides of the battery 76, and that the connector 66 may be provided at other orientations and locations of the detector 22.

In one embodiment, the removable battery 76 includes a button 82 or some other mechanism that enables a user to activate or deactivate the power indicator 80. For instance, a user may press button 82 to turn on the power indicator 80 and may again press the button 82, in turn, to deactivate the power indicator 80. Additionally, the power indicator 80 may, in some embodiments, be automatically deactivated via a timer.

Moreover, in some embodiments, the power indicator 80 may provide an indication that the remaining power of the battery 76 has fallen to or below a threshold level, such as ten percent or twenty percent power remaining. For example, when the remaining power of the battery 76 is below such a threshold, the power indicator 80 may flash or change color to signal to a user to change the battery 76. Additionally, in some embodiments, upon depletion of the battery charge below the threshold, the digital detector 22 may communicate with the system controller 28 to cause some other component of the imaging system 34 to communicate the battery status to a user. For example, a visual indicator may be provided on a display screen of the operator interface 32 or some other component of the imaging system 34, or some component of the imaging system 34 may output an audio signal, such as one or more beeps, to notify the user of the battery condition.

Still further, in one embodiment, the digital detector 22 may be configured to automatically turn itself off after a specified period of inactivity or following completion of an image acquisition procedure when the remaining power of the battery 76 falls below the aforementioned threshold, or below an additional threshold. In such an event, image data acquired by the digital detector 22 may be stored within a memory device 70 provided as part of the detector 22 or a removable battery 76 prior to deactivation of the digital detector 22. In one such embodiment, such stored data may be later communicated from the digital detector 22 upon installation of a charged battery 76 or a tether, as generally discussed below. The battery 76 and/or the connector 66 may include locking features 84 that facilitate the retention of the battery 76 by the connector 66. As will be appreciated, any suitable locking features, such as one or more sets of mating latches and recesses, may be employed in full accordance with the present techniques. In the presently illustrated embodiment, the digital detector 22 includes a release mechanism 86, such as a spring-loaded switch, that facilitates locking and unlocking of the battery 76 to the connector 66 to facilitate removal of the battery 76 from the digital detector 22.

As noted above, in certain embodiments the removable battery 76 may include a wireless transceiver 88 and/or a memory device 70. In such embodiments, data acquired by the detector 22 may be wirelessly transmitted to the detector controller 26 via the wireless transceiver 88 provided on the removable battery 76. In embodiments in which a memory 70 is also provided on the removable battery (or on the detector 22 itself), data may be written to the memory 70 in the event that no wireless data connection can be established or when signal strength is below a desired level. In such an embodiment, upon establishment of a suitable wireless connection, the acquired image data may be wirelessly transmitted to the detector controller 26.

The imaging system 34 may also include a battery charging station 96 configured to recharge one or more batteries 76 for the digital detector 22. It is noted that, for embodiments in which the batteries 76 are user-removable from the digital detector 22, a depleted battery 76 may be removed from the digital detector 22 and replaced with a charged battery 76. This, in turn, enables continued operation of the detector 22 (with the newly installed, charged, battery 76) with minimal downtime (e.g., the time needed to replace a battery), while also enabling the depleted battery 76 to be recharged, such as by the battery charging station 96, independent of the detector 22.

The battery charging station 96 may be attached to the portable X-ray unit 36 or may be provided elsewhere in the imaging system 34. In the presently illustrated embodiment, the battery charging station 96 includes several slots 98 configured to receive removable battery 76. As can be appreciated, each slot 98 may include electrical connections that mate with those of a respective battery 76 to enable recharging of the battery 76. A power indicator 100 may be provided for each slot 98 for generally indicating the level of charge on the associated battery 76. Although the presently illustrated battery charging station 96 includes slots for recharging up to three batteries 76, it is noted that other embodiments may allow for charging a different number of batteries. In one embodiment, once a particular battery 76 is fully charged, the battery charging station 96 will automatically turn off the charging current for that particular battery 76.

As noted above, a battery 76 may be removed from the connector 66 of the digital detector 22 and a tether 104 may be coupled in its place, as generally illustrated in FIGS. 7 and 8 in accordance with one embodiment. In the presently illustrated embodiment, the tether 104 includes a plug 106 that may be inserted into the connector 66, as generally indicated by reference numeral 108. A cable portion 110 of the tether 104 may provide operating power to the digital detector 22. Additionally, in at least some embodiments, data acquired by the digital detector 22 may be communicated to other components of the imaging system 34 via the cable 110. In some embodiments, the tether 104 may enable wired communication providing higher data transmission rates than that supported via wireless communication, and a user may choose between wired or wireless communication based on desired data transfer rates, ergonomic considerations, and the like. The tether 104 may also include locking features 84 that facilitate the retention of the tether 104 by the connector 66. The release mechanism 86 may be used to disengage the tether 104 from the connector 66 in a manner similar to that discussed above with respect to removal of the battery 76 from the connector 66.

In embodiments in which the tether provides power to the detector 22 and data transfer from the detector 22, the cable 110 may include conductors for power and data. For example, in one embodiment, the cable 110 may include two pairs of conductors for power, four pairs of conductors for data transfer in accordance with 100 bT Ethernet protocols, two conductors for determination that the detector 22 is present using a suitable connection confirmation technique, and so forth. In one embodiment, the cable 110 may be provided as a small and flexible cable, such as a cable that is less than 10 mm in diameter, such as 7 mm in diameter.

In one embodiment, the tether 104 of the plug 106 may be a rotating tether 112 that allows a radial range of motion for the cable 110. For example, in certain embodiments, the rotating tether 112 may allow a range of rotation of 45°, 90°, 120°, 150°, 180°, 210°, or anywhere between these ranges. Such a rotating tether 112 may decrease the bend radius in instances where the tether 104 might otherwise be crimped or severely bent when placed under the patient. For example, in such instances, the rotating tether 112 may rotate in the direction of the tension, thereby reducing the stain on the tether 104 and/or preventing reversed bending. Turning to FIGS. 9-11, various views of a plug 106 with a rotating tether 112 are depicted. As depicted in these views, in one embodiment, the rotating tether may include a strain relief 114 that rotates and that prevents crimping or bending of the cable 110 at the rotating tether 112.

The rotating tether 112 may also include a hub 116 through which all or part of the cable 110 passes to enter the plug 106. The hub 116 may be constructed as a single piece or may be constructed as two or more pieces that may be assembled to form the hub 116.

In one embodiment, the hub 116 may include a hole through which a hinge or pin functioning as an axis may pass to allow rotation of the hub 116 and the rest of the rotating tether 112 relative to the remainder of the plug 106. In another embodiment, the hub 116 may include a circular region 118 which may be received in a complementary region 120 of the plug 106 to allow rotation of the hub 116 and the rest of the rotating tether 112 relative to the remainder of the plug 106. In yet other embodiments, slip rings may be employed to allow rotation of the rotating tether. Further, in other embodiments, the rotating tether may be rotatable in more than one dimension, e.g., in x and y dimensions instead of just x, thereby reducing cable strain in more than one dimension. For example, in one embodiment, a ball joint may be employed to allow rotation of the rotating tether 112 in more than one dimension.

As generally depicted in FIG. 12, image data may be acquired by, and communicated from, a digital detector 22 in accordance with a method 124 of one embodiment. The method 124 may include exposing (block 126) the detector 22 to radiation, such as from the radiation source 12. The method 124 may also include generating image data (block 128) based on the received radiation.

In the depicted embodiment, the data generated by the detector 22 may be transmitted or otherwise provided to a detector controller 26 or other component of the imaging system. As depicted in method 124, if a wireless connection is present between the detector 22 and a data receiving components of the imaging system (e.g., detector controller 26), the data may be transmitted wirelessly (block 132) to the data receiving components. For example, in one embodiment, the detector 22 may be powered by a battery 76 that includes a wireless transceiver 88 and/or the detector 22 may itself include a wireless transceiver 88. In such an embodiment, if a suitable wireless connection can be established with the data receiving component and/or if no wired connection is also determined to be present, the image data may be wirelessly transmitted via the wireless transceiver 88 in the battery 76 or the detector 22.

Alternatively, if a wired connection is present between the detector 22 and the data receiving components of the imaging system (e.g., detector controller 26), the data may be transmitted via a wired connection (block 134) to the data receiving components. For example, in one embodiment, the detector 22 may be connected to a detector controller 26 via a plug 106 and cable 110 or by a data transfer cable attached to a docking connector 74. In such an embodiment, the image data may be transmitted via the wired connection to the data receiving components of the imaging system.

If no suitable wired or wireless connection can be established between the detector 22 and the data receiving components of the imaging system (e.g., detector controller 26) or if a delay in the transfer of image data is desired (such as due to low battery power), the image data may be stored (block 136), such as in a memory device 70 provided as part of the battery 76 or the detector 22. In one embodiment, a capacitor may also be provided on the detector 22 to power a storage device in the event that the battery is dead and no communication is available.

It is noted that, in various embodiments, the image data may be stored in the memory device 70 at any suitable time following acquisition, which may include storing the image data prior to, during, or following any attempt to wirelessly communicate the image data. Additionally, the detector 22 or battery 76 may provide an output to indicate to a user that the data has been stored in the memory and is available for subsequent transmission. This output may include a visual output, an auditory output, or both, and may be provided via the power indicator 80 of the battery or LED indicators 72 of the detector or through some other additional output device of the battery 76 or the detector 22.

Technical effects of the invention include the ability to operate a digital detector in a fully-wireless mode or in a tethered mode via installation of a battery or a tether, respectively, in a user-accessible connector of the digital detector. Additionally, a memory device of the battery or digital detector may store data acquired by the digital detector, which may enable retention of the data in the event of power loss (e.g., upon removal of a battery) and communication of the data either via a tether or wirelessly at a subsequent time. In addition, a rotatable tether of a digital detector may allow a connected cable to rotate in one or more dimensions relative to the detector, thereby reducing strain on the cable.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A tether for connecting a portable detector to an imaging system, the tether comprising:
   a cable portion comprising both power conductors configured to transmit power and data conductors configured to transmit medical image data;
   a plug shaped to fit within a battery receptacle of a housing of the portable detector when a battery is not present and to simultaneously connect the data conductors to data line contacts within the battery receptacle and to connect the power conductors to power line contacts within the battery receptacle; and
   a rotatable structure connecting the cable portion to the plug such that the cable portion swivels in at least one-dimension with respect to the plug when the plug is inserted within the battery receptacle.

2. The tether of claim 1, wherein the plug comprises conductors for transmission of both power and medical image data.

3. The tether of claim 1, wherein the plug comprises at least two conductors for power and at least two conductors for medical image data transfer.

4. The tether of claim 1, wherein the cable portion is less than 10 mm in diameter.

5. The tether of claim 1, wherein the rotatable structure allows the attached cable to swivel within a range of rotation of 45°, 90°, 120°, 150°, 180°, 210°, or anywhere there between.

6. The tether of claim 1, wherein the rotating structure comprises a hub configured to interface with a housing of the plug such that the rotating structure rotates with respect to the remainder of the plug.

7. The tether of claim 1, wherein the rotating structure comprises one or more of a slip ring or a ball joint.

8. A digital X-ray detector comprising:
   a detector array configured to generate medical image data based on incident X-ray radiation;
   a housing in which the detector array is disposed; and
   a receptacle within the housing, the receptacle configured to non-simultaneously receive a tether plug and a removable battery, wherein the receptacle includes a connector configured to connect to the tether plug, when present, so as to receive power via two or more electrical contacts present in the connector and to exchange medical image data via two or more data contacts present in the connector and wherein the connector is configured to receive power from the battery, when present, via the two or more electrical contacts present in the connector.

9. The digital X-ray detector of claim 8, comprising a docking connector separate from the receptacle, wherein the docking connector is configured to transmit at least one of medical image data or power via a wired connection.

10. The digital X-ray detector of claim 8, comprising one or more of a wireless transceiver capable of transmitting the generated medical image data or a memory device capable of storing the generated medical image data.

11. A method comprising:
    generating electronic medical image data in response to X-rays incident upon a digital detector array of a digital X-ray detector;

determining whether the digital X-ray detector is coupled to an X-ray imaging system via a wireless connection or a wired connection formed by a tethered plug inserted into a complementary battery receptacle of the digital X-ray detector;

transmitting the electronic medical image data via the wired connection if the wired connection is present;

receiving power for the digital detector array via the wired connection if the wired connection is present;

transmitting the electronic medical image data via the wireless connection if the wireless connection is present and the wired connection is not present; and storing the electronic medical image data on a storage device for later transmission if neither the wired or wireless connection is present.

12. The method of claim 11, wherein transmitting the electronic medical image data via the wired connection comprises transmitting the electronic medical image data via a combined power and data connection formed by the tethered plug inserted into the complementary battery receptacle.

13. The method of claim 11, wherein transmitting the electronic medical image data via the wired connection comprises transmitting the electronic medical image data via a docking connector of the complementary battery receptacle connected to a data transmission line of a cable coupled to the tethered plug.

14. The method of claim 11, wherein storing the electronic medical image data on the storage device includes storing the electronic medical image data on at least one of an optical storage device, a magnetic storage device, or a solid-state memory device.

15. The method of claim 11, wherein storing the electronic medical image data on the storage device includes storing the electronic medical image data in a user-removable storage device.

16. The method of claim 11, wherein transmitting the electronic medical image data via the wireless connection comprises transmitting the electronic medical image data via a wireless transceiver.

* * * * *